United States Patent [19]

Stead et al.

[11] Patent Number: 4,864,018
[45] Date of Patent: Sep. 5, 1989

[54] ANTHRAQUINONE DERIVATIVES AND THEIR USE AS PROTEIN ABSORBENTS

[75] Inventors: Cecil V. Stead, Manchester; Steven J. Burton, Chorley; Christopher R. Lowe, Saffron Walden, all of England

[73] Assignee: Imperial Chemical Industries PLC, London, England

[21] Appl. No.: 885,146

[22] Filed: Jul. 14, 1986

[30] Foreign Application Priority Data

Jul. 15, 1985 [GB] United Kingdom ............... 8517779

[51] Int. Cl.$^4$ .......................................... C07D 251/12
[52] U.S. Cl. .................................. 530/351; 530/359; 530/363; 530/381; 536/1.1; 536/112; 544/187; 544/189; 544/334; 544/335
[58] Field of Search ................ 544/187, 189; 530/351, 530/359, 363, 381

[56] References Cited

U.S. PATENT DOCUMENTS

| 4,016,149 | 4/1977 | Travis | 260/122 |
| 4,355,163 | 10/1982 | Von Oertzen et al. | 544/189 |
| 4,631,341 | 12/1986 | Kayane et al. | 544/189 |

FOREIGN PATENT DOCUMENTS

| 1100587 | 10/1957 | Fed. Rep. of Germany | 544/189 |
| 2657146 | 6/1978 | Fed. Rep. of Germany | 544/189 |
| 2725316 | 12/1978 | Fed. Rep. of Germany | 544/189 |
| 7900541 | 1/1979 | PCT Int'l Appl. | 544/187 |
| 1181744 | 5/1968 | United Kingdom | 544/189 |
| 1540165 | 5/1976 | United Kingdom | 544/187 |

OTHER PUBLICATIONS

Gribnau, T. C. J., *Coupling of Effector Molecules to Solid Supports*, Drukkerij van Mameren B.V.-Nijmegen, The Netherlands, 1977, pp. 22-29, 94-103, 161-181.

Primary Examiner—Mary C. Lee
Assistant Examiner—J. Richter
Attorney, Agent, or Firm—Cushman, Darby & Cushman

[57] ABSTRACT

A compound of the formula:

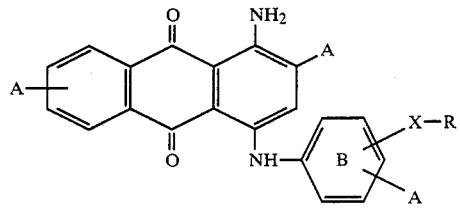

wherein
X is a non-chromophoric bridging group which provides at least three single covalent bonds between Ring B and the group R;
R is a group containing a reactive halogen atom; and
each A independently is H or an acidic group;

provided that the molecule contains sufficient acidic groups to render it water soluble and then when X provides only 3 covalent bonds between Ring B and R, the latter is not a chlorodifuoropyrimidyl group, which is suitable for the preparation of a protein adsorbent or precipitant for use in the separation of mixtures of proteins.

12 Claims, No Drawings

ANTHRAQUINONE DERIVATIVES AND THEIR USE AS PROTEIN ABSORBENTS

This specification describes an invention relating to an anthraquinone (AQ) derivative, and more particularly one carrying a group containing a reactive halogen atom, and to protein adsorbents and precipitants prepared from the anthraquinone derivative which are of value in the separation and purification of proteins.

Cellulose-reactive dyes are well established products which are widely used in the textile industry for the coloration of cotton, viscose and other cellulosic textiles. The molecule of such a reactive dye may be viewed as being made up of two interlinked units, each of which has a different function. One unit is the chromophore whose function is to impart the desired colour and other tinctorial properties to the textile. The other unit is the fibre reactive group which, under well established application conditions, reacts chemically with cellulose to covalently bind the dye molecule to the textile to produce a dyed material which is highly resistant to washing processes.

Whilst cellulose-reactive dyes were initially developed to solve certain problems encountered in the dyeing and printing of cellulosic textile materials, they have, over the years, been found to possess properties, which make them of use outside the textile dyeing field.

It is known, for example from U.S. Pat. No. 4,016,149 and WO 7900541, that these dyes can be attached by similar techniques to carbohydrate substrates, such as agarose, dextrose, dextrans, etc and modified and cross-linked forms thereof. Adducts of such carbohydrate substrates and certain commercially available reactive dyes have been used as adsorbents for the chromatographic separation of certain proteinaceous materials. Amongst the commercial textile dyes which have been used in the manner for protein separation are certain simple blue AQ dyes, such as CI Reactive Blue 2, which has the following formula:

tive dye is that the members are salts, usually sodium salts, of 1-amino-4-arylamino-AQ-2-sulphonic acids, in which the aryl unit is generally a single benzene ring further substituted with a sulphonic acid group and a halogeno-heterocyclic fibre reactive group attached to the benzene ring through an imino group. The monochlorotriazine reactive group present in the dye of Formula A, may be replaced by a different cellulose-reactive halogenoheterocyclic group, such as dichloropyrimidinyl, difluoropyrimidinyl, trichloropyrimidinyl, 5-chlorodifluoropyrimidinyl, 5-cyanodichloro-pyrimidinyl or dichlorotriazinyl, but the preferred reactive group is monochlorotriazinyl.

It has now been found that the selectivity of such adsorbents can be greatly improved by the use of some new AQ derivatives instead of the aforementioned commercial dyes.

According to a first aspect of the present invention there is provided a compound of the formula:

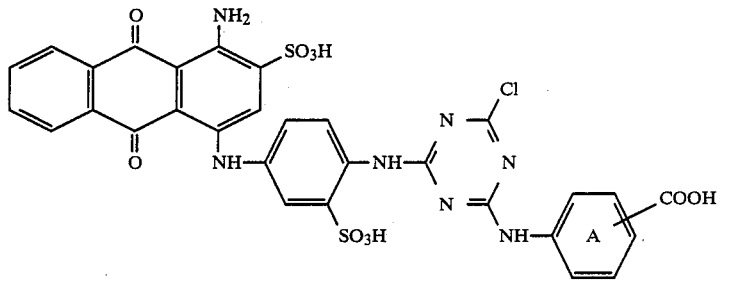

I

The new compound of Formula I has enhanced selectivity for most basic biological species compared with the dye of Formula A. The carboxylate group on a Ring A may be in the ortho, meta or para position with respect to the amino bridge but, it has been found that selectivity is especially enhanced if the carboxylate group is in the meta-position and the compound of Formula I in which the carboxylate group is in the meta-position is a preferred species of this aspect of the invention. The compound of Formula I may be prepared by any of the known methods for preparing the compound of Formula (A) except for the use of an anilinecarboxylate in place of an anilinesulphonate.

According to a second aspect of the present invention there is provided a new compound of the formula:

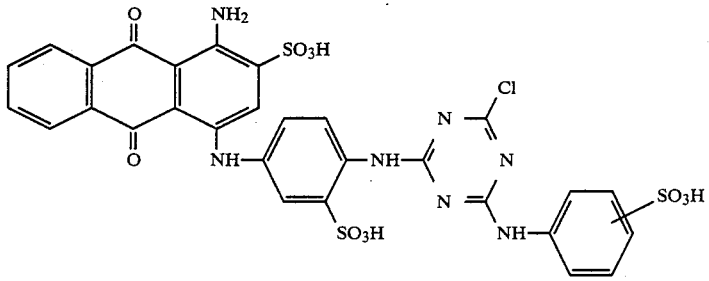

A

Many dyes of this type are found in the ranges of reactive dyes from various dye manufacturers. The molecular characteristic of this class of cellulose reac-

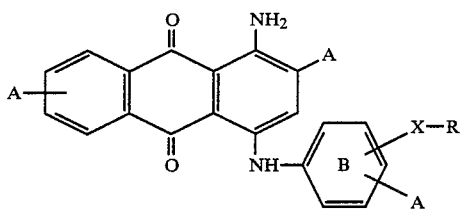

wherein
X is a non-chromophoric bridging group which provides at least three single covalent bonds between Ring B and the group R;
R is a group containing a reactive halogen atom; and each A independently is H or an acidic group;
provided that the molecule contains sufficient acidic groups to render it water soluble and that when X provides only 3 covalent bonds between Ring B and R, the latter is not a chlorodifluoropyrimidyl group.

The bridging group represented by X preferably incorporates a terminal amino group through which it is linked to the group R and more preferably two terminal amino groups through which it is linked to the group R and to Ring B. Thus, preferred forms of X can be represented as:

—Y—NH— and —NH—Y—NH— in which Y is an optionally substituted hydrocarbon group. The group Y may be aliphatic or aromatic and may be substituted by groups which are typically present in dyes, such as $C_{1-4}$-alkyl, $C_{1-4}$-alkoxy, halo, especially chloro, nitro, cyano and acidic groups, e.g. sulpho and carboxyl. The group Y is preferably selected from:
(i) $C_{2-8}$-alkylene, especially polymethylene of the formula:

—(CH$_2$)$_n$— wherein n is from 2 to 8, such as ethylene, propylene or hexamethylene;
(ii) arylene, such as phenylene or 2-sulphophen-1,4-ylene;
(iii) aralkylene, such as 4-methylenephen-1-yl or 4-(eth-2-ylene)phen-1-yl; and
(iv) aralkenylene, such as 4(ethen-2-ylene)-3-sulphophen-1-yl.
It is preferred that the group Y is free from covalent double bonds.

Such bridging groups allow the AQ nucleus to move more freely with respect to the group P than when the Ring B is attached to the group R through a simple amino group, —NH—, as is the case with commercially available cellulose reactive dyes. It is especially preferred that the bridging group, X, is an alkylenediamino group of the general formula:

—HN—(CH$_2$)$_n$—NH—   III in which n is from 2 to 8, especially ethylene-1,2-diamino.

It is preferred that the bridging group, X, provides up to 10, more preferably from 4 to 10, and especially preferably from 4 to 6 single covalent bonds between Ring B and the group R.

The group, R, containing an activated halogen atom is conveniently a cellulose reactive group of the type used to fix cellulose reactive dyes to cellulosic textile materials. Examples of such groups as dichloropyrimidinyl, difluoropyrimidinyl, trichloropyrimidinyl, 5-chlorodifluoropyrimidinyl, 5-cyanodichloropyrimidinyl and dichlorotriazinyl and an especially preferred reactive group is a monochlorotriazine group of the formula:

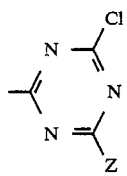

wherein Z is an optically substituted amino group. The optionally substituted amino group represented by Z is preferably an arylamino group, in which the aryl group is optionally substituted mono- or bi-cyclic, preferably carbocyclic, such as phenyl or naphthyl, and carries at least one, and preferably from 1 to 3, water-solubilising acidic group, such as sulphonate or carboxylate, preferably the latter. It is also preferred that the acidic group is in the meta position with respect to the amine link. Other substituents for the arylamino group are preferably selected from halogen, $C_{1-4}$-alkyl, $C_{1-4}$-alkoxy, OH and $NO_2$. It is especially preferred that Z is 3-carboxyphenylamino.

The acidic groups represented by A are required to confer water-solubility and are preferably sulphonate or carboxylate groups and it is preferred that the AQ nuclelus carries only one such group in the 2 position. There should, therefore, be sufficient of these, including an acidic groups on Ring B or in R, to render the whole molecule water-soluble. The compound of Formula II preferably carries from 1 to 4, and more preferably 2 or 3, acidic groups.

An especially preferred compound in accordance with Formula II is:

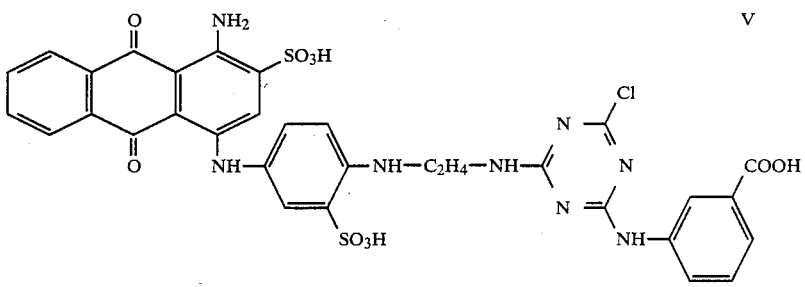

The compound of Formula II, wherein X is —NH—Y—NH— or —Y—NH— may be prepared by condensing a 1-amino-4-bromo-AQ, such as 1-amino-2-sulpho-4-bromo-AQ, with a compound of the formula:

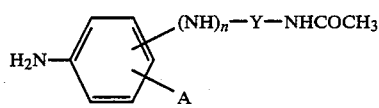

wherein Y is as hereinbefore defined and n is 0 or 1, such as, 5-amino-2-(acetylaminomethyl)benzene sulphonic acid or 5-amino-2-(2-acetylamino-ethylamino)-benzene sulphonic acid, in the presence of a copper catalyst, removing the —COCH$_3$ group from the resulting adduct by hydrolysis, and successively condensing cyanuric chloride with the adduct and with ammonia or an amine, especially an arylamine, such as 3-aminobenzoic acid.

The compounds of Formulae I, II and V have especially good affinities for proteins and thus are adapted for the preparation of protein absorbents and precipitants as hereinafter defined.

According to a third aspect of the present invention there is provided an absorbent comprising the adduct of a compound of Formula I or Formula II and a substrate having a group capable of reaction with the reactive chlorine atom in said compound. The substrate may be a substantially water-insoluble, solid support or a water-soluble polymer. As examples of the solid support there may be mentioned acrylic polymers and co-polymers, silica, titania, alumina, hydroxyalkylmethacrylates, porous glass, but the preferred water-insoluble solid support is a polymeric substrate having a plurality of hydroxyl groups to which the compound of Formula I or Formula II may become attached through the cellulose reactive group. Especially suitable substrates are carbohydrates and modified carbohydrates. Examples of a suitable carbohydrate substrate are agarose, crosslinked agarose, dextrose, dextrans, and modified versions thereof, such as are available as "Sepharose" and "Sephadex" gels ("Sepharose" and "Sephadex" are trade marks of Pharmacia Fine Chemicals) and are described in GB 1,540,165 (Cutter). Other polymeric substrates are polyamides and polyacrylamides. Especially preferred substrates are agarose and crosslinked agarose.

The adsorbent comprising a dye bound to a solid support may be in the form of a column for chromatographic separation purposes or in the form of a membrane to allow separation to be carried out in a membrane separation format.

As examples of water-soluble polymers which may be reacted with dyes of Formula I or Formula II there may be mentioned dextran or polyethylene glycols, the products of the reaction being used to separate protein materials in an aqueous two-phase partition process.

The adsorbents disclosed in accordance with the third aspect of the present invention may be prepared by standard techniques, for example, by reacting a compound of Formula I or II with the carbohydrate substrate in the presence of an acid binding agent, such as an alkali metal hydroxide or carbonate, e.g. NaOH or Na$_2$CO$_3$. Methods for the preparation of such adsorbents and chromatographic columns containing them are well documented, see for example WO 7900541 and U.S. 4,016,149.

According to a fourth aspect of the invention there is provided a protein precipitant comprising an adduct of two or more molecules of an AQ compound of Formula I or Formula II, and a poly-functional linking compound having two or more groups capable of reaction with the reactive halogen present in the AQ compound. Such an adduct can be used to precipitate a protein by aggregation, the adduct acting as a bridge between the protein molecules. The adduct can be formed by reacting two or more molecules of the dye with the poly-functional linking compound. Examples of di-functional linking compounds are alkylene diamines such as ethylenediamine, propylenediamine, tetramathylene diamine and hexamethylenediamine which may be condensed with compounds of Formula I or II with the elimination of the elements of hydrogen chloride. Examples of linking compounds with a high functionality are polyaminoalkanes such as diethylene triamine, triethylenetetramine and tetraethylene pentamine which can link together more than two molecules of Formula I or II.

The adsorbents and precipitants as described herein derived from the AQ derivative of Formula II have greatly enhanced binding efficiency for certain biological molecules such as proteins and enzymes, especially enzymes such as nicotinamide nucleotide-dependent oxido-reductases; phosphokinases; coenzyme-A dependent enzymes; hydrolases; acetyl-, phosphoribosyl- and amino-transferases; RNA and DNA nucleases and polymerases; restriction endonucleases; synthetases; hydroxylases; and a number of proteins such as serum albumin; clotting and complement factors; phytochrome; lipoproteins; and interferon, when compared with the compound of Formula A and are thus especially well adapted for the separation of such species from mixtures of proteins.

Examples of enzymes and proteins to which the adsorbents and precipitants of the present invention are especially adapted for binding are alcohol dehydrogenase (horse liver), lactase dehydrogenase (rabbit muscle), serum albumin (human blood), and chymotrypsin (bovine pancreas).

The present invention is further illustrated by the following examples in which all parts and percentages are by weight unless otherwise indicated.

EXAMPLE 1

A solution of 13.3 g of the disodium salt of 1-amino-4-(4-aminoanilino)-anthraquinone-2,3'-disulphonic acid in 200 g of water was cooled below 5° C. and run into an ice cold suspension of 4.65 g of cyanuric chloride in 100 g of water. During the addition, and for 1 hour thereafter, the pH was maintained between 6 and 7 by the the addition of 2N Na$_2$CO$_3$ as required and the temperature kept below 5° C. To the solution was then added 3.8 g of 3-aminobenzoic acid and the temperature raised, to and maintained, at 40° C. for two hours during which 2N Na$_2$CO$_3$ was added as required to maintain a pH of between 6.5 and 7. To the solution was then added 30 g of NaCl and the mixture cooled below 5° C. The precipitated trisodium salt of 1-amino-2-sulpho-4-(3-sulpho-4-[2-chloro-4-(3-carboxyanilino)-1,3,5-triazin-6-ylamino]anilino)-AQ was filtered off and dried in vacuo.

EXAMPLE 2

To a solution of 30 g of anhydrous Na$_2$CO$_3$ in 100 g of water were added 8 g of the sodium salt of 1-amino-4-bromo-anthraquinone-2-sulphonic acid and 7.7 g of 4-(2-acetylaminoethylamino)aniline-3-sulphonic acid. The mixture was stirred and 3.8 g of CuSO$_4$.5H$_2$O added, followed by 1.6 g of zinc dust. The mixture was stirred for 26 hours at 45°–50° C. and then diluted to a volume of 400 ml with water and adjusted to pH 7 with 35% HCl. The mixture was then heated to 95° C., filtered hot and the disodium salt of 1-amino-4-(4-[2-acetylaminoethylamino]-3-sulphoanilino)-anthraquinone-2-sulphonic acid precipitated from the filtrate by the addition of 120 g of salt.

The above precipitate was dissolved in 500 g of water and the pH lowered to 0.5 by the addition of 35% HCl. The solution was stirred for two hours at 95° C. and the precipitate of the mono-sodium salt of 1-amino-4-(4-[2-amino-ethylamino]-3-sulphoanilino)anthraquinone-2-sulphonic acid filtered off, washed with 1000 g of acetone and dried at 50° C.

A solution of 2.4 g of cyanuric chloride in 20 g of acetone was added to 100 g of water cooled below 5° C. and a neutralised solution of 1.68 g of 3-aminobenzoic acid in 100 g of water run into the suspension over 10 minutes, the pH being maintained at 6–7 throughout the addition and for 30 minutes subsequently. A neutral solution of the 7 g of the disodium salt of 1-amino-4-(4-[2-aminoethylamino]-3-sulphoanilino)-anthraquinone-2-sulphonic acid was added and the mixture heated for three hours at 40° C., the pH being maintained between 8 and 9 during this time by the addition of 1M NaOH, as required. To the solution were added 40 g of NaCl and the precipitate filtered off, washed with 1000 g of acetone and dried in vacuo. There was obtained the trisodium salt of 1-amino-4-(4-[2-(2-chloro-4-[3-carboxyanilino]-s-triazin-6-ylamino)-ethylamino]-3-sulphoanilino)-anthraquinone-2-sulphonic acid as a dark powder giving a blue solution in water.

EXAMPLE 3

In a similar manner, the trisodium salt of 1-amino-4-(4-[2-(2-chloro-4-[3-carboxyanilino]-s-triazin-6-ylamino)-hexylamino]-3-sulphoanilino)-anthraquinone-2-sulphonic acid was prepared by replacing the 4-(2-acetylaminoethylamino)aniline-3-sulphonic acid used in Example 2 by the equivalent weight of 4-(2-acetylaminohexylamino)aniline-3-sulphonic acid.

EXAMPLE 4

In a similar dyestuff the trisodium salt of 1-amino-4-(4-[-3-(2-chloro-4-[3-carboxyanilino]-s-triazin-6-ylamino)-5-carboxyphenylamino]-3-sulpho-phenylamino)-anthraquinone-2-sulphonic acid was prepared by replacing the 4-(2-acetylaminoethylamino)aniline-3-sulphonic acid used in Example 2 by the equivalent weight of 4-amino-3'-acetylamino-5'-carboxydiphenylamine-2-sulphonic acid.

EXAMPLE 5

To a solution of 100 g of anhydrous Na$_2$CO$_3$ in 500 g of water were added 40 g of the sodium salt of 1-amino-4-bromo-anthraquinone-2-sulphonic acid and 272 g of 4,4'-diaminodiphenyl-2,2'-disulphonic acid. The mixture was stirred and 3.8 g of CuSO$_4$.5H$_2$O added, followed by 1.6 g of zinc dust. The mixture was stirred for 3 hours at 65° C. and then diluted by the addition of 1000 g of water, heated to 95° C., filtered hot and 300 g of NaCl added to the filtrate. After cooling below 5° C. the mixture was again filtered to remove precipitated 4,4'-diaminodiphenyl-2,2'-disulphonic acid and 100 g of concentrated hydrochloric acid added to the filtrate. The precipitated disodium salt of 1-amino-4-(4-[4-amino-2-sulphophenyl]-3-sulphoanilino)-anthraquinone-2-sulphonic acid was filtered off, redissolved in 250 g of water and again precipitated by the addition of 50 g of NaCl, filtered off again and dried at 50° C.

A solution was prepared by dissolving 22.7 g of the disodium salt of 1-amino-4-(4-[4-amino-2-sulphophenyl]-3-sulphoanilino)anthraquinone-2-sulphonic acid in 400 g of water and the pH of the solution adjusted to 7. The solution was cooled below 5° C. and 6.7 g of cyanuric chloride added. The mixture was stirred below 5° C. and the pH maintained between 6 and 7 during four hours by the addition of 35 g of 1M NaOH. To the mixture were added 4.6 g of 3-aminobenzoic acid. The temperature of the mixture was then raised to, and held at, 40° C. for four hours whilst the pH was maintained between 6 and 7 by the addition of 70 g of 1M NaOH. At the end of this period the product was precipitated by the addition of 70 g of NaCl to the solution. The precipitate of the tetrasodium salt of 1-amino-4-(4-[4-(2-chloro-4-[3-carboxyanilino]-s-triazin-6-ylamino)-2-sulphophenyl]-3-sulphoanilino)-anthraquinone-2-sulphonic acid was filtered off and dried at 50° C.

Further dyestuffs of the invention were prepared in a similar manner by replacing the 272 g of 4,4'-diaminodiphenyl-2,2'-disulphonic acid used in Example 4 by the equivalent weight of the diamine listd in Column I of Table 1.

TABLE 1

| Example | Diamine |
|---|---|
| 6 | 4,4'-diaminostilbene-2,2'-disulphonic acid |
| 7 | 4,4'-diaminodiphenylmethane |
| 8 | 4,4'-diaminodiphenylamine-2,3'-disulphonic acid |

EXAMPLE 9

A solution was made by dissolving 41.6 g of the sodium salt of 4-anilino-1-aminothraquinone-2-sulphonic acid in 450 g of 98% H$_2$SO$_4$ and this was added 17.7 g of N-methylolphthalimide. The solution was stirred overnight and poured onto 1500 g of ice and the precipitate filtered off. The precipitate was resuspended in 200 g of water, and after adjusting the pH to 8, 400 g of NaCl were added and the precipitate filtered.

The filtered precipitate was stirred with a mixture of 1000 g of water and 1000 g of ethanol and 10 g of hydrazine hydrate were added. After refluxing for an hour, the solution was filtered and the ethanol removed from the filtate by evaporation. To the residual aqueous solution were added 100 g of NaCl and the precipitate of the sodium salt of 1-amino-4-(4-aminoethylanilino)-anthraquinone-2-sulphonic acid filtered off and dried at 50° C.

To an ice cold solution of 3.9 g of sodium metanilate in 200 g of water were added 4 g of cyanuric chloride. The mixture was stirred for 30 minutes whilst maintaining the temperature below 5° C. and the pH between 6 and 7 by the addition of a 1M NaOH. To the mixture were added 8.9 g of the sodium salt of 1-amino-4-(4-aminomethylanilino)-anthraquinone-2-sulphonic acid and the suspension diluted by the addition of a further 300 g of water. The suspension was then heated to 40° C. and maintained at this temperature whilst keeping the pH between 8 and 9 by the addition of 1M NaOH as required, over three hours. After completion of the reaction 50 g of NaCl were added and the precipitate of the disodium salt of 1-amino-4-[2-chloro-4-(3'-sulphoanilino)-s-triazin-6-yl-aminomethyl]-anilino)- anthraquinone-2-sulphonic acid was filtered off and dried.

EXAMPLE 10

Three dyes of Formula I, in which the COOH group on Ring A is in the ortho (o), meta (m) and para (p) positions respectively, (i), (ii) and (iii) in Table 2, and three analogues in which the COOH groups are replaced by SO₃H groups, (iv), (v) and (vi) in Table 2, were assessed by affinity of binding with horse liver alcohol dehydrogenase. The assessment procedure comprised measuring the reduction in rate of enzyme de-activation by CI Reactive Blue 4 (a highly reactive, dichlorotriazine dye which rapidly deactivates horse liver alcohol dehydrogenase) when of dyes (i) to (vi) was allowed to compete with CI Reactive Blue 4 for the enzyme. From the reductions in rate observed the dissociation constants, $K_D$, of the [enzyme-dye] combinations were calculated and these values are listed in Table 2. In comparing the results, the smaller $K_D$ value observed for each carboxylate analogue, (i), (ii) and (iii) indicates that the binding affinity of each of these dyes is markedly and surprisingly higher than that of the corresponding sulphonate analogue, (iv), (v) and (vi), respectively.

TABLE 2

|      | I        | $K_D$ |
|------|----------|-------|
| (i)  | o-COOH   | 11    |
| (ii) | m-COOH   | 4     |
| (iii)| p-COOH   | 30    |
| (iv) | o-SO₃H   | 14    |
| (v)  | m-SO₃H   | 17    |
| (vi) | p-SO₃H   | 96    |

In Table 2, the compound (iv) and a mixture of compounds (v) and (vi) are commercially available and commonly used for the preparation of chromatography columns for protein separation purposes. The above values for dissociation constants show that in this application compounds of general formula I and having a carboxylate substituent on the ring A are much more suited for this purpose.

EXAMPLE 11

A glass mini-column (0.5 cm by 10 cm) was packed with 1 g (wet weight) of a proprietary brand of agarose (Sepharose 4B) to which approximately 2 micromoles of the compound of Formula I, having a m-COOH group on ring A, had been bound by the conventional method and the column bed equlibrated with HEPES/-NaoH buffer having a pH value of 7.5. To this column was applied 0.2 g of a solution of crude horse liver alcohol dehydrogenase, containing about 3 units of enzyme, and after 10 minutes the column was washed with 6 g of the equilibration buffer at a flow rate of 30 g.h⁻¹.cm⁻². The adsorbed horse liver alcohol dehydrogenase was then eluted at 25° C. with 20 g of eluent having a linear NADH gradient ranging from 0 to 0.2 mM. Purified enzyme showing, an assay, a five fold purification was recovered in 64% yield.

EXAMPLE 12

The compound of Formula V was reacted with an excess of 1,6-diaminohexane to form the analogue in which the chlorine atom on the triazine ring was replaced by a 6-aminohexylamino group. This analogue was attached to a proprietary brand of agarose (Sepharose 4B) which had previously been activated by carbonyldiimidazole in the conventional manner. A glass mini-column (0.5 cm by 10 cm) was packed with 1 g (wet weight) of the resulting gel, having a dye concentration of 2 micromoles/g. The column bed was equilibrated with HEPES/NaOH buffer having a pH value of 7.5. To this column was applied 0.2 g of a solution of commercially pure horse liver alcohol dehydrogenase, containing about 3 units of enzyme, and after 10 minutes the column was washed with 6 g of the equilibration buffer at a flow rate of 30 g.h⁻¹.cm⁻². The adsorbed horse liver alcohol dehydrogenase was then eluted at 25° C. with 20 g of eluent having a linear NADH gradient ranging from 0 to 0.2 mM. This procedure resolved the enzyme into two distinct fractions which re-chromatographed as homogeneous entities. Both of the fractions were surprisingly shown to consist of a mixture of EE and EE' isoenzymes but, nevertheless, had markedly different enzyme activity, the second fraction having approximately four times the enzyme activity of the first fraction.

We claim:

1. A compound of the formula:

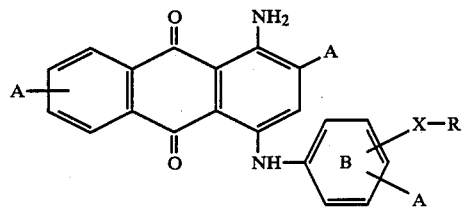

wherein

X is —NH—Y—NH— wherein Y is selected from $C_{2-8}$-alkylene, mono- or bi-homocyclic arylene, monocyclicarylene-$C_{1-4}$-alkylene or monocyclicarylene-$C_{1-4}$ alkenylene;

R is dichloro-triazinyl and monochlorotriazinyl of the formula:

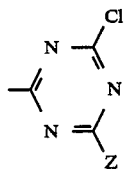

Z is a phenylamino or naphthylamino; and each A independently is H or an acidic group;

provided that the molecule contains sufficient acidic groups to render it water soluble.

2. A compound according to claim 1 wherein X is is ethylene-1,2-diamino.

3. A compound of claim 1 wherein Z is 3-carboxyphenylamino.

4. The compound of the formula:

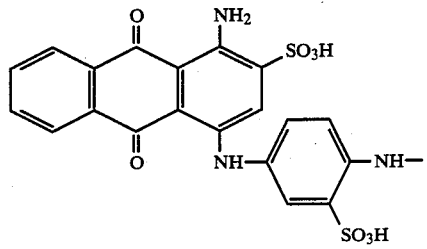

-continued

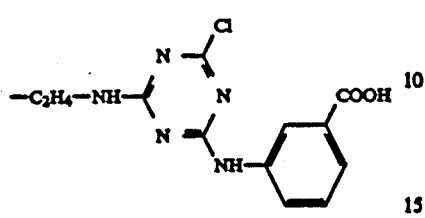

or a water-soluble sat thereof.

5. A compound of the formula:

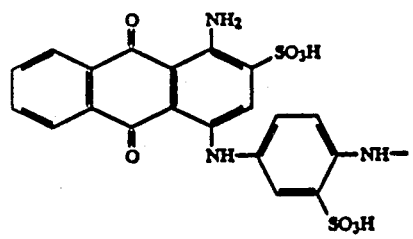

-continued

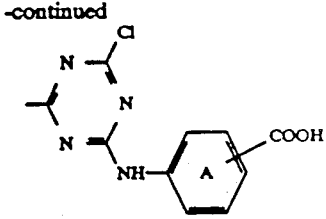

or a water-soluble salt thereof.

6. A compound according to claim 5 wherein the carboxylate group on Ring A is in the meta position with respect to the amino bridging group.

7. A protein adsorbent comprising the adduct of a compound according to claim 1 and a substrate having a group capable of reaction with the the chlorine atom present in R.

8. A protein adsorbent according to claim 7 wherein the substrate is water-insoluble, solid support or a water-soluble polymer.

9. A protein adsorbent according to claim 8 wherein the support is a carbohydrate.

10. A protein adsorbent comprising an adduct of the compound of claim 6 with a polymer or co-polumer of agarose.

11. A protein precipitant comprising an adduct of two or more molecules of an anthraquinone compound according to claim 1 and a polyfunctional linking compound containing at least two groups reactive with the the chlorine atom present in R.

12. A protein precipitant according to claim 10 wherein the polyfunctional linking compound is selected from ethylenediamine, propylenediamine, tetramethylenediamine, diethylenetriamine, triethylenetetramine and tetraethylenepentamine.

* * * * *